United States Patent [19]

Jaeb et al.

[11] Patent Number: 4,899,760
[45] Date of Patent: Feb. 13, 1990

[54] NOISE REJECTING DETECTOR FOR BIOMEDICAL SIGNALS

[75] Inventors: Jonathan P. Jaeb, San Antonio; Merle E. Converse, Helotes, both of Tex.

[73] Assignee: Colin Electronics Co., Ltd., Komaki, Japan

[21] Appl. No.: 62,781

[22] Filed: Jun. 15, 1987

[51] Int. Cl.[4] ............................................. A61B 5/04
[52] U.S. Cl. ................................... 128/696; 128/901; 128/902
[58] Field of Search ............... 128/630, 668, 695, 696, 128/633, 634, 672, 673, 901–902, 904; 364/417

[56] References Cited

U.S. PATENT DOCUMENTS

| | | | |
|---|---|---|---|
| 4,223,682 | 9/1980 | Sherman | 364/417 |
| 4,245,648 | 1/1981 | Trimmer et al. | 128/672 |
| 4,245,650 | 1/1981 | Welker et al. | 128/696 |
| 4,407,290 | 10/1983 | Wiber | 128/633 |
| 4,416,288 | 11/1983 | Freeman | 364/417 |
| 4,461,301 | 7/1984 | Ochs | 128/630 |
| 4,461,302 | 7/1984 | Phillipps et al. | 128/630 |
| 4,623,248 | 11/1986 | Sperinde | 128/634 |

*Primary Examiner*—Francis Jaworski
*Assistant Examiner*—George Manuel
*Attorney, Agent, or Firm*—Matthews & Branscomb

[57] ABSTRACT

An improved biological signal detector which is extremely sensitive, yet resistant to the effects of high frequency noise. A multiplexed signal representation of a plurality biological signals is demultiplexed by a detector circuit comprising a plurality of switches each of which controls an individual storage network. A switch logic control circuit synchronizes the various switches to close during the time intervals corresponding to the pulse amplitudes representing the particular signal of interest. The amplitude of the alternating component of each of the biological signals is stored in one of the respective storage networks over a number of pulse time intervals. In the preferred embodiment, the storage networks of the detector each have a time constant which is purposely chosen to be substantially longer than the time interval of the pulses. The long time constant of the storage networks allows the detector circuit to track changes in amplitude which manifest themselves over a relatively large number of time intervals, but prevents the detection of high frequency noise signals which may be present during the sampling intervals.

8 Claims, 4 Drawing Sheets

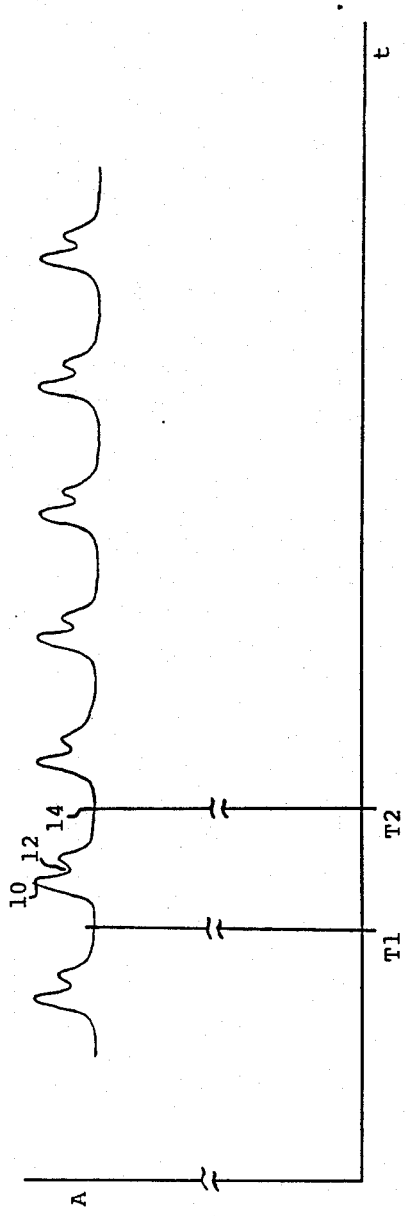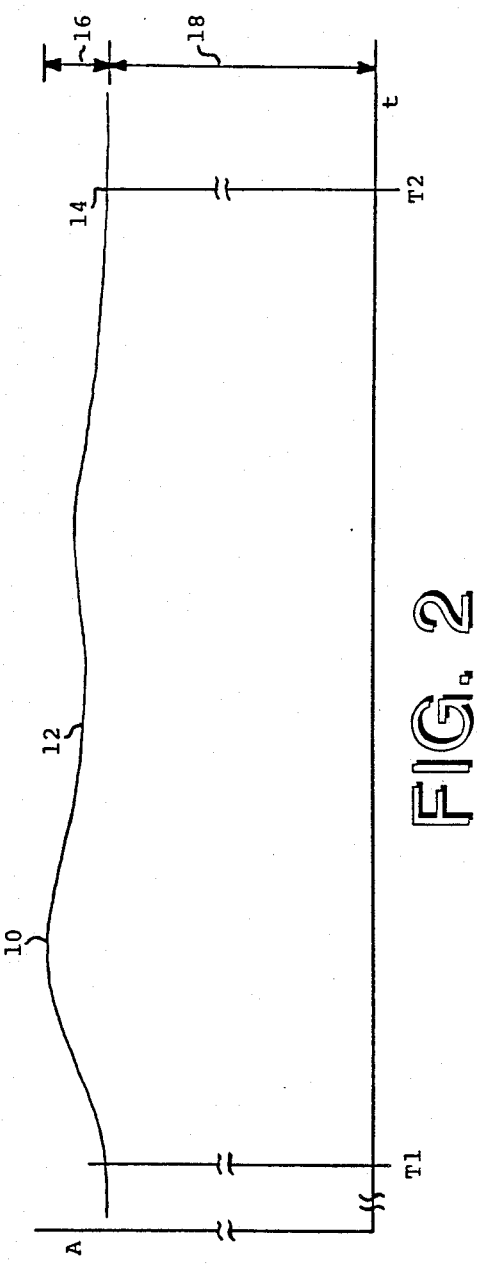

NOISE REJECTING DETECTOR FOR BIOMEDICAL SIGNALS

FIELD OF THE INVENTION

The present invention relates generally to detectors for use in biomedical monitoring systems. Specifically, the present invention provides an improved low noise, high sensitivity detector for use on biomedical monitoring equipment, such as systems used to measure blood pressure or to estimate the degree of oxygen saturation in blood.

BACKGROUND

In the field of biological signal monitoring, one is generally interested in signals that are closely related to the operation of the patient's heart. Such signals tend to have a number of common characteristics: (1) they tend to occur in the frequency range below 30 hertz; (2) they are generally at a very low level; (3) they are often associated with high levels of background noise; and (4) they are generally susceptible to the effects of motion-related artifacts.

In recent years, there has been a trend toward the development of biomedical monitoring equipment requiring acquisition and processing of multiple waveforms having the characteristics discussed above. Examples of systems requiring multiple waveforms include those for indirect measurement of blood pressure and those for indirect measurement of blood oxygen saturation. U.S. Pat. No. 4,269,193 issued to Eckerle and U.S. Pat. No. 4,423,738 issued to Newgard disclose noninvasive indirect measurement devices in which a plurality of pressure waveforms are processed to monitor blood pressure on a continuous basis. U.S. Pat. No. 4,407,290 issued to Wilber discloses an example of a system whereby light transmitted through an appendage at different wavelengths is used to determine the patient's arterial blood oxygen saturation.

In applications such as those discussed above, the biological signals of interest generally comprise a pulsatile waveform which is synchronous with the patient's heartbeat and which often includes harmonics of up to 20 hertz. The pulsatile component of the signal rides on a nonpulsatile component which may or may not be of interest, depending on the specific application. In situations where these signals are readily available, in continuous form, and at fairly high levels, they can be monitored using techniques which are known in the art. In some applications, however, these signals are only available in non-continuous form. For example, in the case of an optical oximeter, alternating pulse signals produced by light sources at different wavelengths are multiplexed onto a single line. In such systems, it is necessary to de-multiplex and reconstruct the signals. Most systems based on the acquisition of signals of this type employ commercially available sample-and-hold circuits which are followed by band-pass filters. These sample-and-hold circuits lack the extreme accuracy that is often required for acquisition of low-level biological signals. In addition, conventional sample-and-hold circuits tend to be sensitive to high frequency noise and often pass this noise into the system, thus corrupting the signal of interest.

The effectiveness of biological signal monitoring systems can be enhanced significantly by an improved detector which overcomes the problems discussed above. Specifically, there is a need for a detector circuit which is capable of acquiring very low level signals with a high degree of accuracy and which is relatively insensitive to high frequency noise signals.

SUMMARY OF THE INVENTION

It is an object of the present invention to overcome the difficulties of the prior art by providing an improved biological signal detector which is extremely sensitive, yet resistant to the effects of high frequency noise. In the preferred embodiment, a plurality of biosensors are used to obtain an electrical representation of the alternating component of the pulsatile portion of biological signals of interest. Conventional control circuitry is employed to cause the individual biosensors to sample a particular biological signal during predetermined time intervals to obtain a sequence of non-continuous pulse amplitude signals representing the amplitude of the biological signal. The signal detected by each biosensor during the sampling interval is comprised of a direct current component, an alternating component at a first frequency and an alternating current noise signal component at a second frequency. The noncontinuous amplitude signals produced by each of the biosensors during the respective time intervals are combined to produce a multiplexed signal representation of the plurality of biological signals.

In the preferred embodiment of the invention, the multiplexed signal representation of the biological signals is demultiplexed by a detector circuit comprising a plurality of switches each of which controls an individual storage network. A switch logic control circuit synchronizes the various switches to close during the time intervals corresponding to the pulse amplitudes representing the particular signal of interest. The amplitude of the alternating component of each of the biological signals is stored in one of the respective storage networks over a number of pulse time intervals. In the preferred embodiment, the storage networks of the detector each comprise a resistor and capacitor having an RC constant which is purposely chosen to be substantially longer than the time interval of the pulses. The long time constant of the storage networks allows the detector circuit to track changes in amplitude which manifest themselves over a relatively large number of time intervals, but prevents the detection of high frequency noise signals which may be present during the sampling intervals. The present invention, therefore, provides a detector which can accurately monitor changes in the amplitude of a biological signal, but which is insensitive to the effects of high frequency noise signals.

BRIEF DESCRIPTION OF THE DRAWINGS

FIG. 1 is a graphical representation of a typical pulse waveform produced by a human heart.

FIG. 2 is a time expanded graphical representation of one pulse of the waveform shown in FIG. 1.

DETAILED DESCRIPTION OF THE PREFERRED EMBODIMENT

Figure 3:
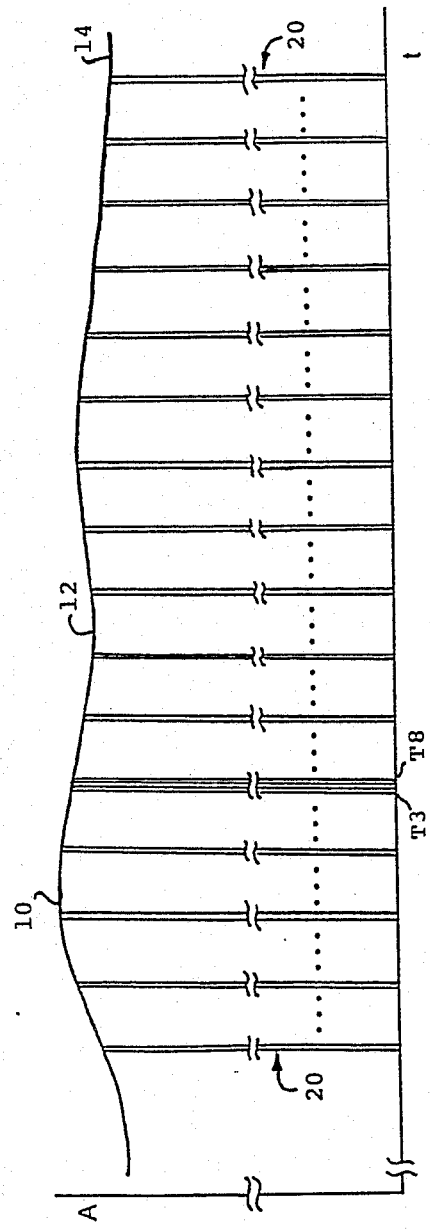
FIG. 3 is an illustration of a plurality of sampling intervals used to obtain a series of pulse amplitude representations of the waveform shown in FIG. 2.

Referring to the drawings in more detail, and to FIG. 1 in particular, a graphical representation is shown of the pulse waveform of a biological signal related to the operation of the human heart. Each of the pulses is characterized by a systolic peak 10, a dicrotic notch 12 and a diastolic minimum 14. As was discussed above, modern noninvasive monitoring equipment is typically based on the acquisition of a plurality of waveforms of the type shown in FIG. 1. For example, a noninvasive reflectance oximeter determines blood oxygen saturation by comparing the pulse signals related to the amount of light reflected at two different wavelengths. A pulse waveform of the type shown in FIG. 1 must be detected for the reflected light corresponding to each of the wavelengths. The changes in the detected signals as a function of time can be correlated with the degree of oxygen saturation of the blood contained in the patient's tissue. For a non-invasive blood pressure monitoring system, such as that shown in U.S. Pat. No. 4,269,193 issued to Eckerle, a plurality of pressure sensitive elements are utilized, with each of the pressure sensing elements producing an output similar to that shown in FIG. 1.

The biological signal shown in FIG. 1 comprises an alternating current (AC) component and a direct current (DC) component. FIG. 2 is a time-expanded graphical representation of the pulse occurring between time periods T1 and T2 of FIG. 1. The amplitude of the AC component of the signal is shown by reference number 16, while the amplitude of the DC component of the signal is shown by reference number 18. The relative amplitudes of each of these components depends on the location at which the signal is obtained and on the specific type of biomedical sensor used. For example, the signal obtained from the bio-sensor used in a reflectance oximeter may have a DC component on the order of 3 volts and an AC component on the order of 3 millivolts. The signal produced by an individual bio-sensor for a continuous blood pressure monitoring system may be on the order of 1 volt AC and 3 volts DC.

FIG. 3 is a graphical representation of a plurality of sampling intervals used to sample the biological signal shown in FIG. 2 in order to obtain a representation of the amplitude of the AC component of the signal. The specific sampling rate is dependent on a number of factors. However, a sampling rate of approximately 1000 hertz is commonly used to obtain a representation of a biological signal having a frequency between 20 and 150 beats per minute. The typical time interval for each of the pulse sampling intervals is on the order of 10 to 100 microseconds for most biological signal detection circuits.

Figure 4:
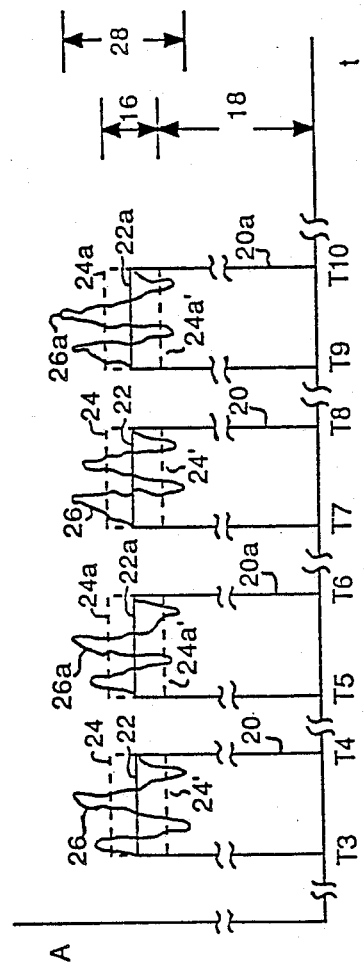
FIG. 4 is a graphical representation of a time series pulse train obtained by sampling the amplitude of a plurality of biological signals such as the one shown in FIG. 3.

FIG. 4 is a graphical representation of a series of pulses obtained by sampling a plurality of biological signals such as those shown in FIGS. 1–3. In particular, the pulses shown in FIG. 4 are representative of the type of pulse amplitude signals which could be obtained from biosensors used in an optical oximeter system. For example, the pulses 20 occurring during time intervals T3–T4 and T7–T8 could correspond to detected light at one wavelength, e.g. 660 nanometers, while the pulses occurring during time intervals T5–T6 and T9–T10 could correspond to detected light at a second wavelength, e.g. 880 nanometers. Referring again to FIG. 3, the two non-continuous pulses 20 occurring during the time interval T3–T8 are shown as adjacent pulses. Because the sample rate is high in comparison to the frequency of the biological signal, the AC amplitude of the signal will change slowly during this time interval. However, a significant quantity of high frequency noise can be present during this time interval. For example, significant signal detection problems can be created by electrical noise having a frequency ranging from a few kilohertz to several megahertz.

For a monitoring system such as an optical oximeter, the duty cycle of the light sources can be as low as two percent. Thus the time interval between successive pulses will be very large in comparison to the time interval of the individual pulses. In other monitoring systems, such as noninvasive blood pressure monitoring systems, the time interval between adjacent pulses can be very short. The biomedical signal detector of the present invention, described in greater detail below, is effective for eliminating high frequency noise from the detected biological signals for either of these systems.

The relative amplitudes of the AC component 16 and DC component 18 of a single pulse sample is shown generally in FIG. 4. The DC level which must be detected by the circuit is illustrated by the voltage level 22, while the time-varying AC component is illustrated by the dashed lines 24 and 24'. In many circumstances the detection of the AC component of the signal is complicated by high frequency noise signals such as that illustrated by waveforms 26 in FIG. 4. Such noise signals often have a bandwidth 28 greater than the amplitude 16 of the AC signal of interest.

Figure 5:
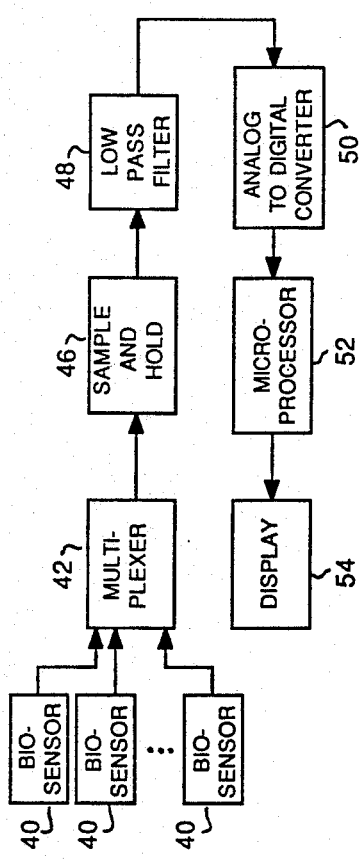
FIG. 5 is a schematic block diagram of a simplified embodiment of a typical biological signal detection circuit.

A conventional biological signal detection circuit is shown generally in the simplified block diagram of FIG. 5. The circuit is broadly comprised of a plurality of bio-sensors 40 to sample the biological signals and produce a plurality of pulse trains similar to those shown in FIGS. 3 and 4. The sampling rate of the bio-sensors 40 depends on the specific application and can be controlled by conventional circuitry known in the art. The respective pulse trains are multiplexed in multiplexer 42 to produce a time-division multiplexed representation of the signals of interest. In conventional detection circuits, a sample-and-hold circuit 46 is used to determine the amplitude of the series of pulses representing the respective signals. The output of the sample and hold circuit 46 is filtered in a low pass filter circuit 48 to smooth and reconstruct the respective signal waveforms. The signal waveform is then processed by the analog-to-digital converter 50 to provide a data signal which can be processed by the microprocessor 52 and displayed on an appropriate display device 54.

Figure 5A:
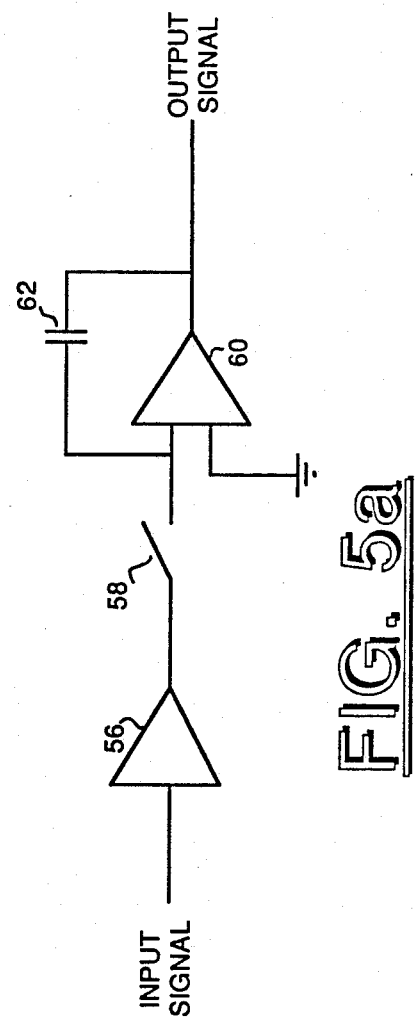
FIG. 5a is a schematic diagram of a typical sample-and-hold circuit used in a conventional biological signal detection circuit.

A conventional detection circuit such as that shown in FIG. 5 is unsuitable for obtaining an accurate indication of the signal components illustrated in FIG. 4. In particular, most conventional biological signal detectors employ sample-and-hold circuits 46, of the type illustrated generally in FIG. 5a. The circuit is comprised of an input buffer 56, a switch 58, an output buffer 60 and a storage element 62. During the sampling interval, the switch 58 is closed and the amplitude of the signal is stored in the storage element 62. The design parameters of the amplifiers 56 and 60 and the storage element 62 are generally chosen such that the signal acquisition time of the circuit is much less than the time interval during which the signal is being sampled. In other words, a conventional sample-and-hold circuit is designed to acquire the signals shown in FIG. 4 during a short sample time, e.g. T3–T4, which is usually on the order of 10 to 100 microseconds. A sample-and-hold circuit which is able to acquire the signal in this period of time will also have a very high bandwidth. The wide bandwidth of the circuit allows the circuit to track high frequency noise which is present during the sample interval. As a result, the high frequency noise, for example the noise signal 26 shown in FIG. 4, is stored with the signal during the hold interval T4–T7. Because T4–T7 is comparatively long, the high frequency noise is, in effect, converted into a lower frequency signal which is within the passband of the desired biological signal. This low frequency noise signal tends to corrupt the biological signal of interest. Removal of the high frequency noise prior to the sample-and-hold circuit is not possible because of the multiplexed nature of the signals. A filter would mix the signals together, rather than separate them.

For the reasons discussed above, the sample-and-hold circuit used in conventional detectors is unsuitable for use in monitoring equipment requiring extremely high levels of accuracy. For example, effective operation of a reflectance oximeter requires that the AC component of the reflected signals must be detected within an accuracy of 0.001 percent in order to keep the error terms of the algorithms within acceptable limits. A conventional sample-and-hold circuit, such as that described above cannot be used to detect the desired signal within the required level of accuracy.

Figure 6:
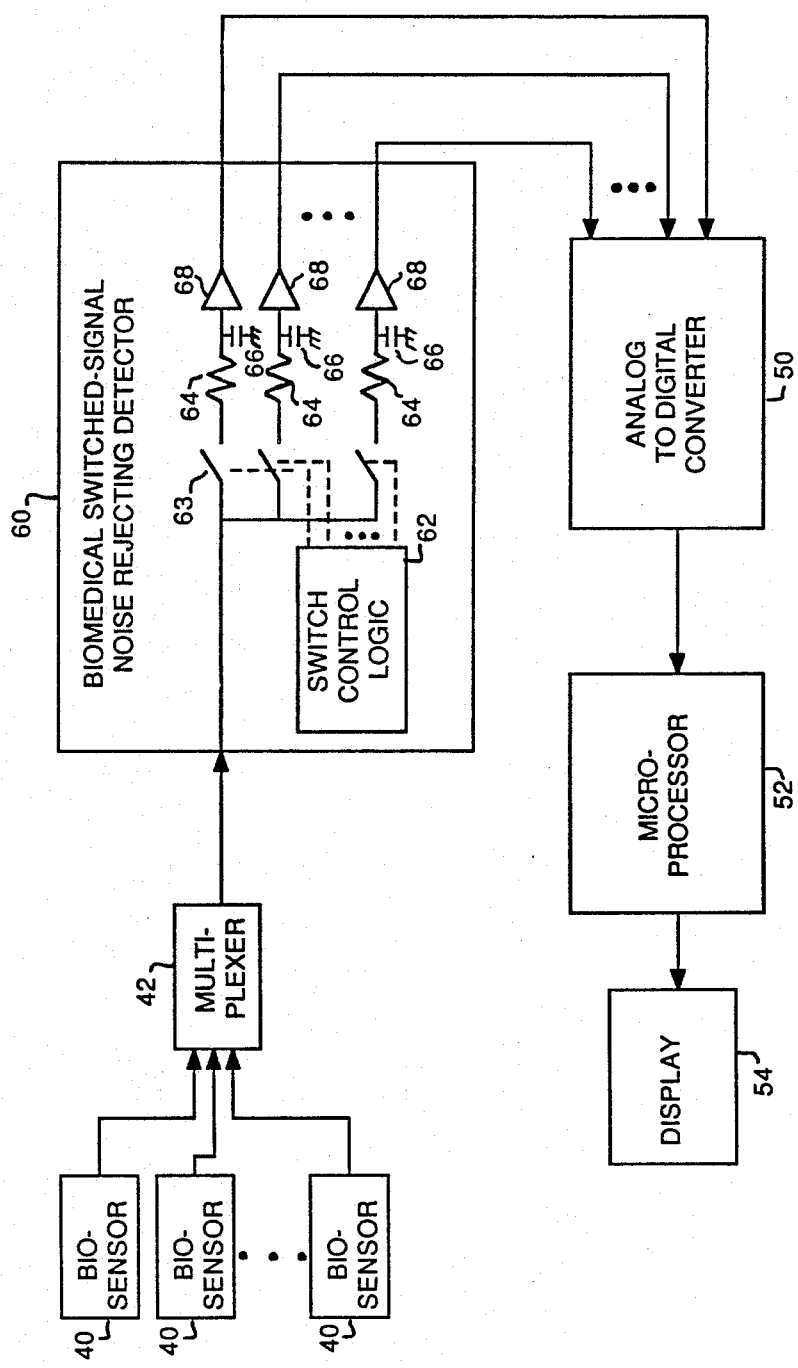
FIG. 6 is a schematic block diagram of a simplified embodiment of the noise rejecting detector for biological signals of the present invention.

The difficulties discussed above are overcome by the improved biological signal detector shown in FIG. 6. The invention detector circuit contains many of the system components discussed above, but replaces the conventional sample-and-hold circuit with a switched signal noise rejecting detector circuit 60. The detector circuit 60 comprises a switch control logic circuit 62 which is synchronized with the timing cycle of the multiplexed pulse train provided by the multiplexer 42. This switch control logic closes the individual analog switches 63 during the sample interval of the individual pulses representing the signals of interest, for example, T3–T4 and T7–T8 of FIG. 4. In the circuit provided by the present invention, the amplitude representation of the pulse signal is stored in a storage network defined by resistor 64 and capacitor 66. The values of these components are purposely chosen to have an RC time constant significantly greater than the time interval during which the pulse width of interest is sampled, e.g., T3–T4 of FIG. 4. The RC network is followed by an input buffer 68 having a high input impedance in order to avoid discharging the capacitor 66 during the hold interval. In the preferred embodiment, one switched storage network is provided for each of the signals produced by the biosensors.

The detector of the present invention acquires the biological signal at a very slow rate and effectively filters the signal while sampling. The individual channels of the detector circuit 60 effectively integrate the signal during the time interval corresponding to the pulse width, e.g., T3–T4, and hold this value during the time interval between pulses, e.g., T4–T7. The final value stored during one time interval becomes the initial value for the next time interval corresponding to a particular biological signal, e.g. T7 of FIG. 4. After a number of pulses, the voltage on the capacitor will have risen to the value of the signal pulses. Once this point has been reached, the capacitor 66 will not charge any further. As the value of the signal increases or decreases over time, the capacitor will charge or discharge accordingly. It is important to note that because of the time constant of the RC network, the voltage across the circuit will only follow slow moving changes in pulse amplitude. In other words, the circuit will only follow changes in amplitude that manifest themselves over a series of pulses, such as those having a frequency in the range produced by biological signals. Because of the relatively long time constant of the RC network, the detector circuit 60 does not track high frequency noise signals, such as that illustrated by the signal waveform 26 in FIG. 4. Instead, the high frequency noise detected by the bio-sensors along with the desired biological signal is effectively filtered out during the sample interval. For example, in an optical oximeter employing the detector of the present invention, the pulse amplitude is acquired over a period of approximately 20 pulses.

The analog switch 63 in each of the detection channels of the switched-signal detection circuit 60 is closed at a rate corresponding the duty cycle of the signal of interest, thus allowing the circuit to be used on multiplexed signals. Because the RC network is active only during the time that the switch 63 is closed, the cutoff frequency of the circuit is the usual $F_{co} = \frac{1}{2}RC$, but rather is $F_{co} = (\text{Duty Cycle})/2RC$, where the duty cycle is that of the analog switch. In one possible embodiment of the detector of the present invention, the storage network has a time constant of approximately 5 milliseconds and is used to sample a pulse amplitude signal occurring over a time interval of approximately 10 microseconds. Other time constants can be used for other applications. However, to achieve the noise rejecting characteristics of the invention circuit, it is important that the time constant of the storage network in the detector circuit 60 is substantially longer than the time interval during which the biological signal is sampled.

While the biological signal detector of the present invention has been described in connection with the preferred embodiment, it is not intended to be limited to the specific form set forth herein, but on the contrary, it is intended to cover such alternatives, modifications and equivalents as may be reasonably included within the spirit and scope of the invention as defined by the appended claims.

We claim:
1. A biological signal detector, comprising:
   means for obtaining an electrical representation of a plurality of biological signals related to the operation of a human heart, each said signal comprising a direct current component, an alternating current component at a first frequency, and an alternating current noise signal at a second frequency, said second frequency being substantially higher than said first frequency, said electrical representation of each of said biological signals being defined by a plurality of pulse amplitude signals having predetermined time intervals;
   means for combining said pulse amplitude signals to produce a multiplexed signal comprising an ordered succession of pulses representing each of said biological signals; and means for demultiplexing said multiplexed signal to obtain a representation of each of said respective biological signals, comprising means for storing a value corresponding to a predetermined portion of the amplitude of the individual pulse amplitude signals during each said time intervals, said means for storing being nonresponsive to said noise signal at said second frequency.

2. The detector according to claim 1, said time intervals of said individual pulse amplitude signals being between 10 and 100 microseconds.

3. The detector according to claim 2, said means for storing said portion of said amplitude of said pulse signals comprising a storage network defined by a resistor and a capacitor, said resistor and capacitor having an RC constant significantly longer than the time interval during which said individual pulse amplitude signals are measured.

4. The detector according to claim 3, said storage network defined by said RC network having a time constant of approximately 5 milliseconds.

5. A method for detecting biological signals, comprising the steps of:
obtaining an electrical representation of a plurality of biological signals related to the operation of a human heart, each said signal comprising a direct current component, an alternating current component at a first frequency, and an alternating current noise signal at a second frequency, said second frequency being substantially higher than said first frequency, said electrical representation of each of said biological signals being defined by a plurality of pulse amplitude signals having predetermined time intervals;
combining said pulse amplitude signals to produce a multiplexed signal comprising an ordered succession of pulses representing each of said biological signals;
demultiplexing said multiplexed signal to obtain a representation of each of said respective biological signals, comprising the steps of storing in a storage network a value corresponding to a predetermined portion of the amplitude of the individual pulse amplitude signals during each said time intervals, said storage network being nonresponsive to said noise signal at said second frequency.

6. The method according to claim 5, said time intervals of said individual pulse amplitude signals being between 10 and 100 microseconds.

7. The method according to claim 6, said storage network defined by a resistor and a capacitor, said resistor and capacitor having an RC constant significantly longer than the time interval during which said individual pulse amplitude signals are measured.

8. The method according to claim 7, said storage network defined by said RC network having a time constant of approximately 5 milliseconds.

* * * * *